US012446638B2

(12) United States Patent
Nabai

(10) Patent No.: US 12,446,638 B2
(45) Date of Patent: Oct. 21, 2025

(54) WRAPAROUND EYE SHIELD SYSTEMS AND METHODS

(71) Applicant: LoupeSaver, LLC, Del Mar, CA (US)

(72) Inventor: Sarah Nabai, Del Mar, CA (US)

(73) Assignee: LoupeSaver, LLC, Del Mar, CA (US)

( * ) Notice: Subject to any disclaimer, the term of this patent is extended or adjusted under 35 U.S.C. 154(b) by 0 days.

(21) Appl. No.: 18/373,756

(22) Filed: Sep. 27, 2023

(65) Prior Publication Data

US 2024/0016244 A1 Jan. 18, 2024

Related U.S. Application Data

(63) Continuation-in-part of application No. 18/222,602, filed on Jul. 17, 2023, now abandoned.

(60) Provisional application No. 63/389,541, filed on Jul. 15, 2022.

(51) Int. Cl.
*A41D 13/11* (2006.01)
*A61F 9/02* (2006.01)

(52) U.S. Cl.
CPC ............ *A41D 13/1184* (2013.01); *A61F 9/02* (2013.01)

(58) Field of Classification Search
CPC ....... A41D 13/1184; A61F 9/04; A61F 9/045; A61F 9/02; A61F 9/026
See application file for complete search history.

(56) References Cited

U.S. PATENT DOCUMENTS 2,274,791 A 3/1942 Huggins
2,728,078 A 12/1955 Taylor
4,106,119 A * 8/1978 Taupin .................... A61F 9/045 351/111
4,779,291 A * 10/1988 Russell ................... A61F 9/026 2/440
4,856,535 A * 8/1989 Forbes ............... A41D 13/1184 2/9
4,868,930 A 9/1989 Blackstone
5,000,558 A * 3/1991 Blackstone ............ G02C 5/126 351/111
5,406,943 A * 4/1995 Hubbard ................ A62B 18/08 128/201.17
6,308,711 B1 * 10/2001 Goldberg .................. A61F 9/02 128/858
6,530,659 B1 3/2003 Marcum
7,748,387 B1 * 7/2010 Vu ............................ A61F 9/04 128/858

(Continued)

*Primary Examiner* — Patrick J. Lynch
*Assistant Examiner* — Brianna T. Duckworth
(74) *Attorney, Agent, or Firm* — Acuity IP, LLC; Nathan S. Cassell

(57) ABSTRACT

Wraparound eye shield systems and methods for providing protection to a wearer such as a dental patient. Exemplary eye shield devices include a main panel, an upper panel extending above the main panel, a left lower panel extending below the main panel, a right lower panel extending below the main panel, an upper attachment assembly coupled with the upper panel, a left lower attachment assembly coupled with the left lower panel, and a right lower attachment assembly coupled with the right lower panel. An attachment assembly can include a compressible material, a front adhesive material disposed between a panel and the compressible material, a cover having a plurality of slits, and a rear adhesive material disposed between the compressible material and the cover.

22 Claims, 8 Drawing Sheets

(56) References Cited

U.S. PATENT DOCUMENTS

| | | | | |
|---|---|---|---|---|
| 2006/0143766 | A1 | 7/2006 | Ramsey | |
| 2012/0192330 | A1* | 8/2012 | McMullen | A41D 13/1184 2/9 |
| 2021/0307426 | A1 | 10/2021 | Block et al. | |
| 2024/0016243 | A1 | 1/2024 | Nabai | |

* cited by examiner

WRAPAROUND EYE SHIELD SYSTEMS AND METHODS

CROSS-REFERENCES TO RELATED APPLICATIONS

This application is a continuation-in-part of U.S. patent application Ser. No. 18/222,602 filed Jul. 17, 2023, which claims the benefit of U.S. Provisional Patent Application No. 63/389,541 filed Jul. 15, 2022. The content of each of the applications listed above is incorporated herein by reference.

BACKGROUND OF THE INVENTION

Embodiments of the present invention relate to the field of eye shields, and in particular embodiments, to wraparound eye shield systems and methods.

Eye shields provide protection for a patients' eyes during dental examinations. Although such shields are useful in many situations, still further improvements are desired. Embodiments of the present invention provide solutions to at least some of these outstanding needs.

BRIEF SUMMARY OF THE INVENTION

Embodiments of the present invention include wraparound eye shield systems and methods that can be used to prevent the wearer from having unwanted particles or substances contact their eyes.

In one aspect, embodiments of the present invention encompass wraparound eye shield devices having unique configurations. For example, a wraparound eye shield device can include upper and/or lower sections or flaps that provide protection for the user's eyes.

In another aspect, embodiments of the present invention encompass a wraparound eye shield device that includes a main panel, an upper panel extending above the main panel, a left lower panel extending below the main panel, a right lower panel extending below the main panel, an upper attachment assembly coupled with the upper panel, a left lower attachment assembly coupled with the left lower panel, and a right lower attachment assembly coupled with the right lower panel. In some cases, the upper attachment assembly includes an upper compressible material, an upper front adhesive material disposed between the upper panel and the upper compressible material, an upper cover having a plurality of slits, and an upper rear adhesive material disposed between the upper compressible material and the upper cover. In some cases, the left lower attachment assembly includes a left lower compressible material, a left lower adhesive material disposed between the left lower panel and the left lower compressible material, a left lower cover having a plurality of slits, and a left lower rear adhesive material disposed between the left lower compressible material and the left lower cover. In some cases, the right lower attachment assembly includes a right lower compressible material, a right lower adhesive material disposed between the right lower panel and the right lower compressible material, a right lower cover having a plurality of slits, and a right lower rear adhesive material disposed between the right lower compressible material and the right lower cover. In some cases, the main panel includes a polyester material. In some cases, the upper panel includes a polyester material. In some cases, the left lower panel includes a polyester material. In some cases, the right lower panel comprises a polyester material. According to some embodiments, the main panel, the upper panel, the left lower panel, and the right lower panel are constructed of a single continuous piece of polyester material. According to some embodiments, the upper compressible material comprises a polyurethane foam material. According to some embodiments, the left lower compressible material includes a polyurethane foam material. According to some embodiments, the right lower compressible material includes a polyurethane foam material. According to some embodiments, at least one of the slits of the plurality of slits of the upper cover is a curved slit.

In another aspect, embodiments of the present invention encompass a wraparound eye shield device that includes a main panel, an upper panel extending above the main panel, a left lower panel extending below the main panel, a right lower panel extending below the main panel, an upper attachment assembly coupled with the upper panel, a left lower attachment assembly coupled with the left lower panel, and a right lower attachment assembly coupled with the right lower panel. In some cases, the upper attachment assembly includes an upper compressible material, an upper front adhesive material disposed between the upper panel and the upper compressible material, an upper cover having a plurality of slits, and an upper double coated transfer tape disposed between the upper compressible material and the upper cover. In some cases, the left lower attachment assembly includes a left lower compressible material, a left lower adhesive material disposed between the left lower panel and the left lower compressible material, a left lower cover having a plurality of slits, and a left lower rear double coated transfer tape disposed between the left lower compressible material and the left lower cover. In some cases, the right lower attachment assembly includes a right lower compressible material, a right lower adhesive material disposed between the right lower panel and the right lower compressible material, a right lower cover having a plurality of slits, and a right lower rear double coated transfer tape disposed between the right lower compressible material and the right lower cover. According to some embodiments, the main panel includes a polyester material. In some embodiments, the upper panel includes a polyester material. In some embodiments, the left lower panel includes a polyester material. In some embodiments, the right lower panel includes a polyester material. In some embodiments, the main panel, the upper panel, the left lower panel, and the right lower panel are constructed of a single continuous piece of polyester material. In some embodiments, the upper compressible material includes a polyurethane foam material. In some embodiments, the left lower compressible material includes a polyurethane foam material. In some embodiments, the right lower compressible material includes a polyurethane foam material. In some embodiments, at least one of the slits of the plurality of slits of the upper cover is a curved slit.

DETAILED DESCRIPTION OF THE INVENTION

All illustrations of the drawings are to be describing selected embodiments of the present invention and are not intended to limit the scope of the present invention. All references of user or users pertain to either individual or individuals who would utilize embodiments of the present invention.

Embodiments of the present invention encompass wraparound eye shield systems and methods that can be used by dental patients to prevent unwanted materials from contacting their eyes. Advantageously, exemplary embodiments provide circumferential eye protection for a patient.

Figure 1:
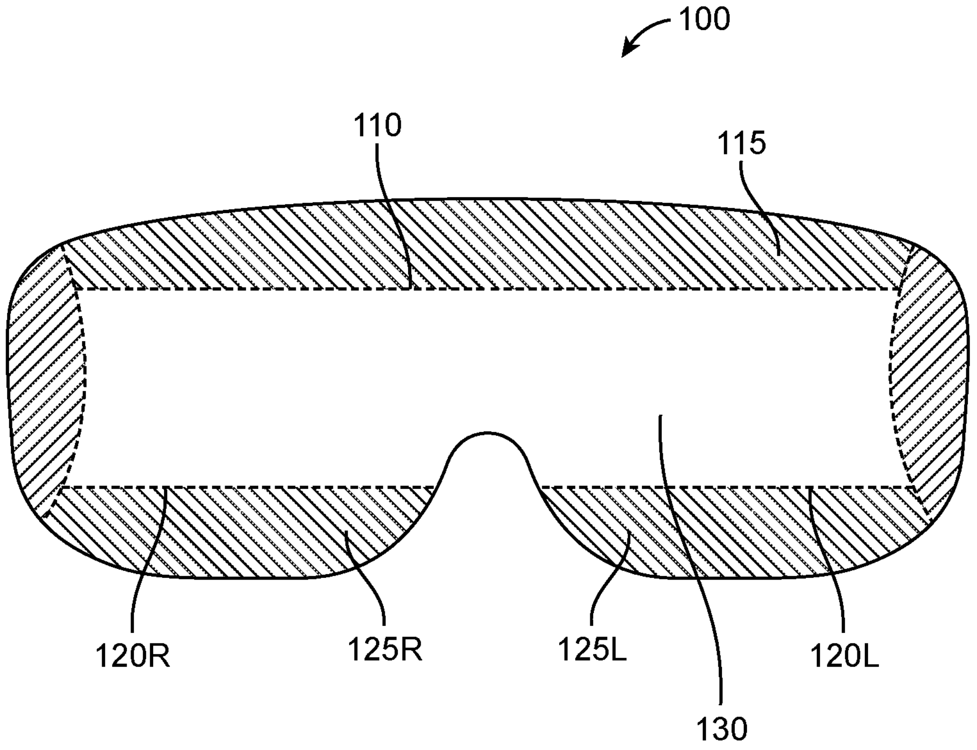
FIG. 1 illustrates aspects of wraparound eye shield systems and methods, according to embodiments of the present invention.

Turning now to the drawings, FIG. 1 shows a wraparound eye shield device 100, according to embodiments of the present invention. As depicted here, eye shield device 100 includes an upper score line 110, a right lower score line 120R, and a left lower score line 120L. In some cases, a score line can be provided as a flexural region or other bendable zone or area. In this way, the device 100 can have an upper flap 115 disposed above the main panel 130, such that the upper flap 115 can bend or curve relative to the main panel 130. Similarly, the device 100 can have two lower flaps 125R and 125L disposed below the main panel 130, such that the lower flaps 125R, 125L can bend or curve relative to the main panel 130. The front side of the device is shown in FIG. 1, in other words the side of the device that faces away from the patient. In some embodiments, device 100 can be provided as a disposable shield.

Figure 2:
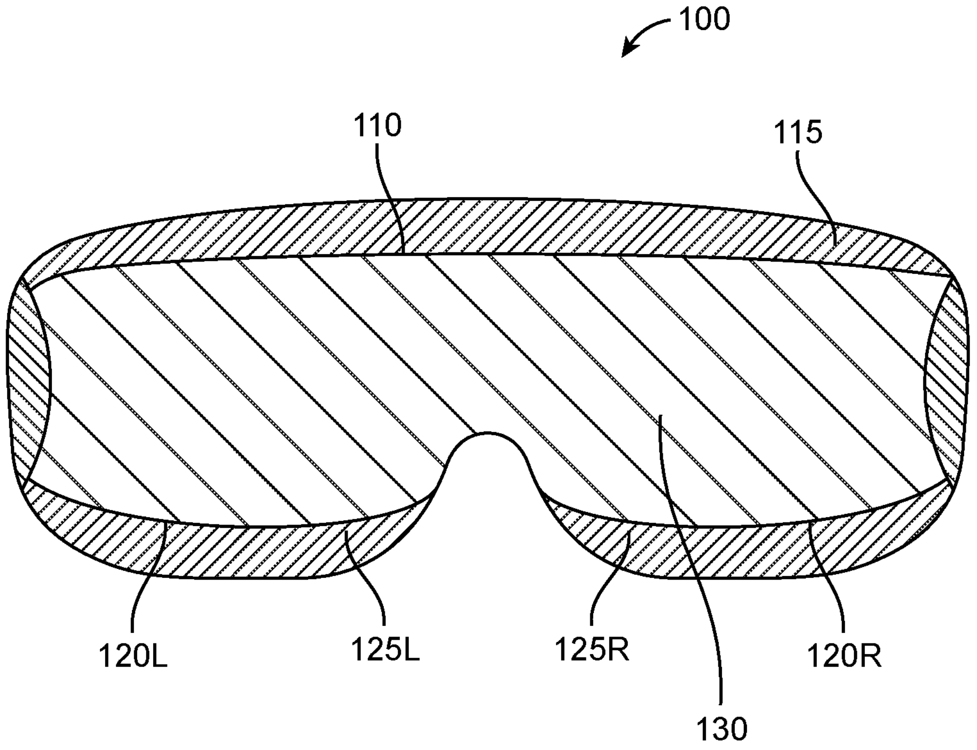
FIG. 2 illustrates aspects of wraparound eye shield systems and methods, according to embodiments of the present invention.

FIG. 2 shows a wraparound eye shield device 100, according to embodiments of the present invention. As depicted here, eye shield device 100 includes an upper score line 110 and lower score lines 120L, 120R. In this way, the device 100 can have an upper flap 115 disposed above the main panel 130, such that the upper flap 115 can bend or curve relative to the main panel 130. Similarly, the device 100 can have lower flaps 125L, 125R disposed below the main panel 130, such that the lower flaps 125L, 125R can bend or curve relative to the main panel 130. The back side of the device is shown in FIG. 2, in other words the side of the device that faces toward the patient.

Accordingly, wraparound eye shield device embodiments of the present invention can provide coverage for the above aspect and/or below aspect for dental patients. Hence, the device can provide enhanced protection for preventing splatter from getting into the patient's eyes, from above and/or below the main panel, for example due to the curved configuration.

Figure 3:
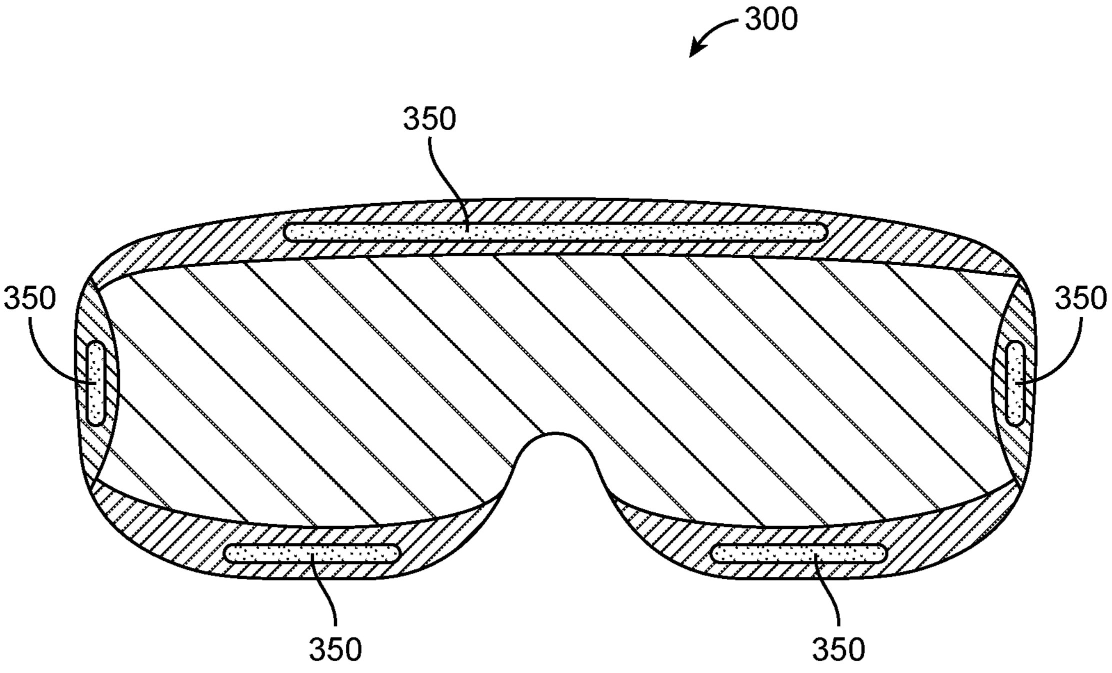
FIG. 3 illustrates aspects of wraparound eye shield systems and methods, according to embodiments of the present invention.

In some cases, as depicted in FIG. 3, a device 300 can include an adhesive material 350 at one or more locations on the shield, for example on the sides of the shield, which can help to minimize a gap between the patient's face and the shield.

Figure 4:
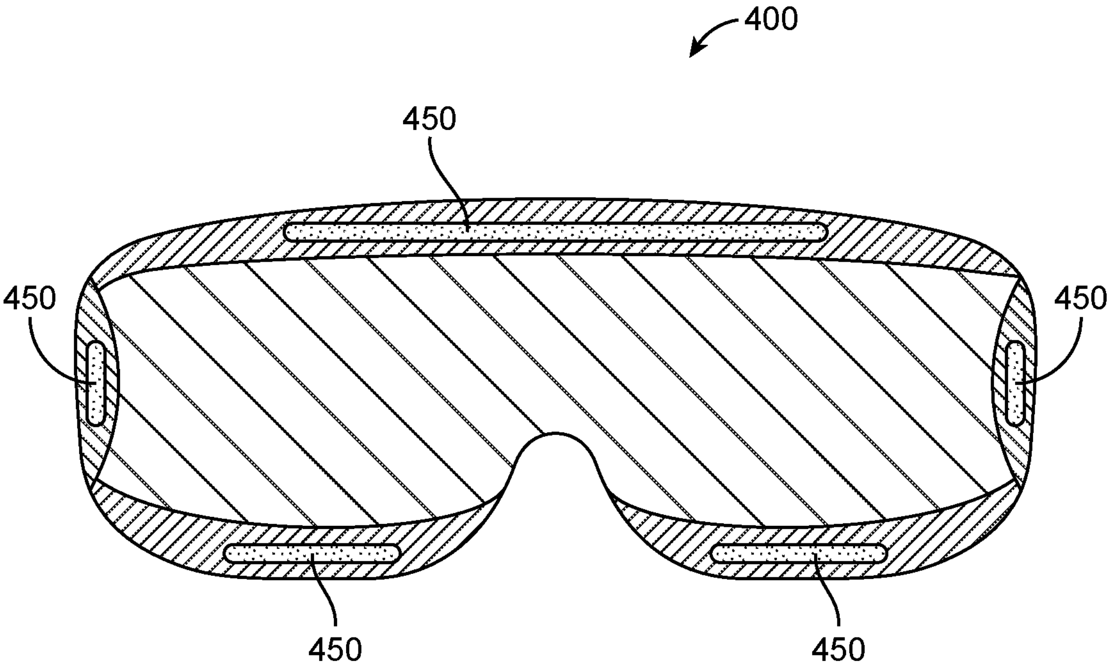
FIG. 4 illustrates aspects of wraparound eye shield systems and methods, according to embodiments of the present invention.

In some cases, as depicted in FIG. 4, a device 400 can include a foam or compressible material 450 at one or more locations on the shield, for example on the sides of the shield, which can help to minimize a gap between the patient's face and the shield.

In some embodiments, a device can include both a foam or compressible material at one more locations on the shield, along with an adhesive material at one or more locations on the foam or compressible material. In some cases, the adhesive material can be located along a portion of or the entirety of an upper foam or compressible material and/or a lower foam or compressible material. In some cases, the foam or compressible material can have a thickness of about ⅜ inch. In some cases, the thickness can have a value within a range from about ¼ inch to about ½ inch. In some cases, the foam or compressible material comprises an open cell foam (e.g. gray).

In some cases, the adhesive material is or includes a medical grade adhesive tape. In some cases, the adhesive material is or includes a direct transfer medical grade tape. The tape or adhesive material can be sticky on both sides, so that it adheres to both the foam and to the wearer's face.

In some cases, there is a slit at one or both end portions of the tape, so as to allow the user or wearer to peel back as needed, to attach the shield with the wearer's face. In some cases, the slit can be on a thin plastic sheet cover that goes over the adhesive (e.g. peel-stick configuration).

In some cases, the shield material is either black (e.g. to block the light) or clear. In some cases, the shield material includes a plastic film. In some cases, the shield material includes polyethylene terephthalate (PET).

Figure 5:
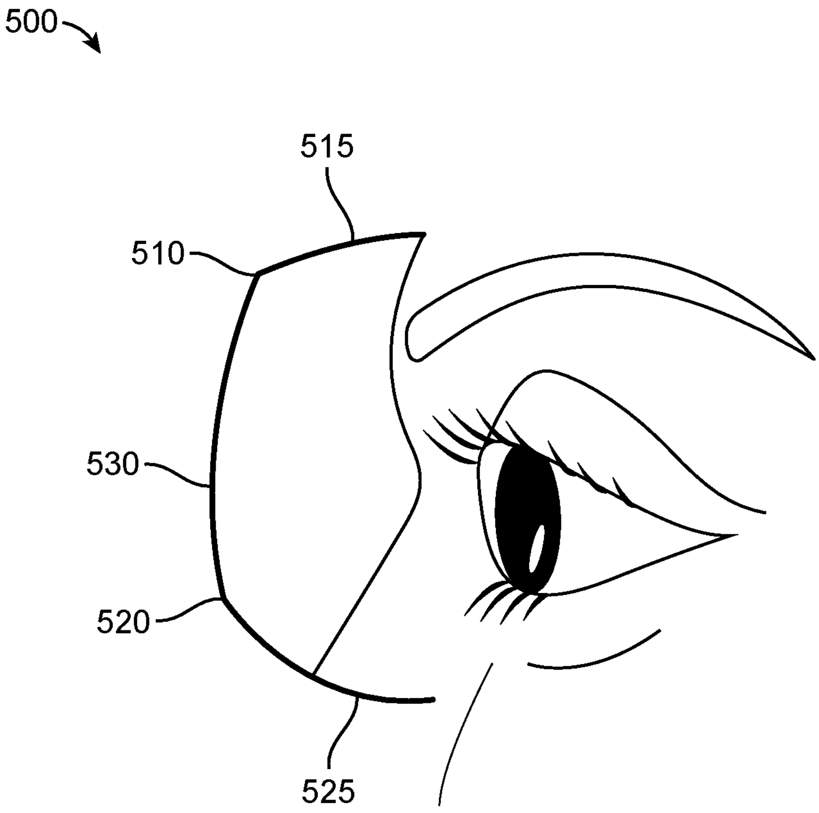
FIG. 5 illustrates aspects of wraparound eye shield systems and methods, according to embodiments of the present invention.

FIG. 5 provides a side view of a wraparound eye shield device 500 according to embodiments of the present invention. As shown here, device 500 includes a main panel 530, an upper panel 515, and a lower panel 525 (which could either be a lower right panel or a lower right panel). Upper score line 510 and lower score line 520 facilitate or enable the curved configuration of the device 500.

Figure 6A:
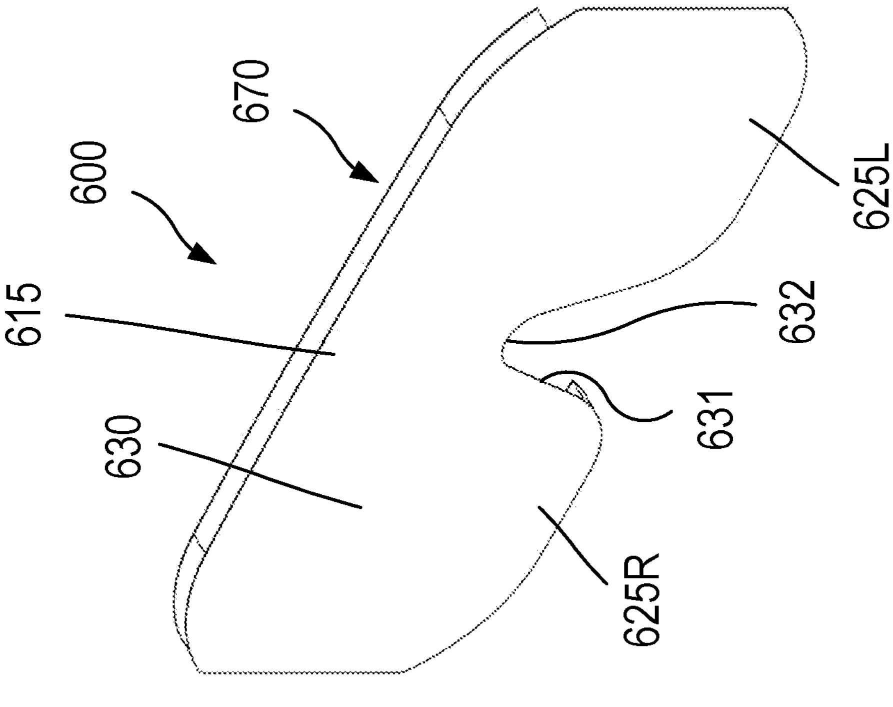
FIGS. 6A and 6B illustrate aspects of wraparound eye shield systems and methods, according to embodiments of the present invention.
Figure 6B:
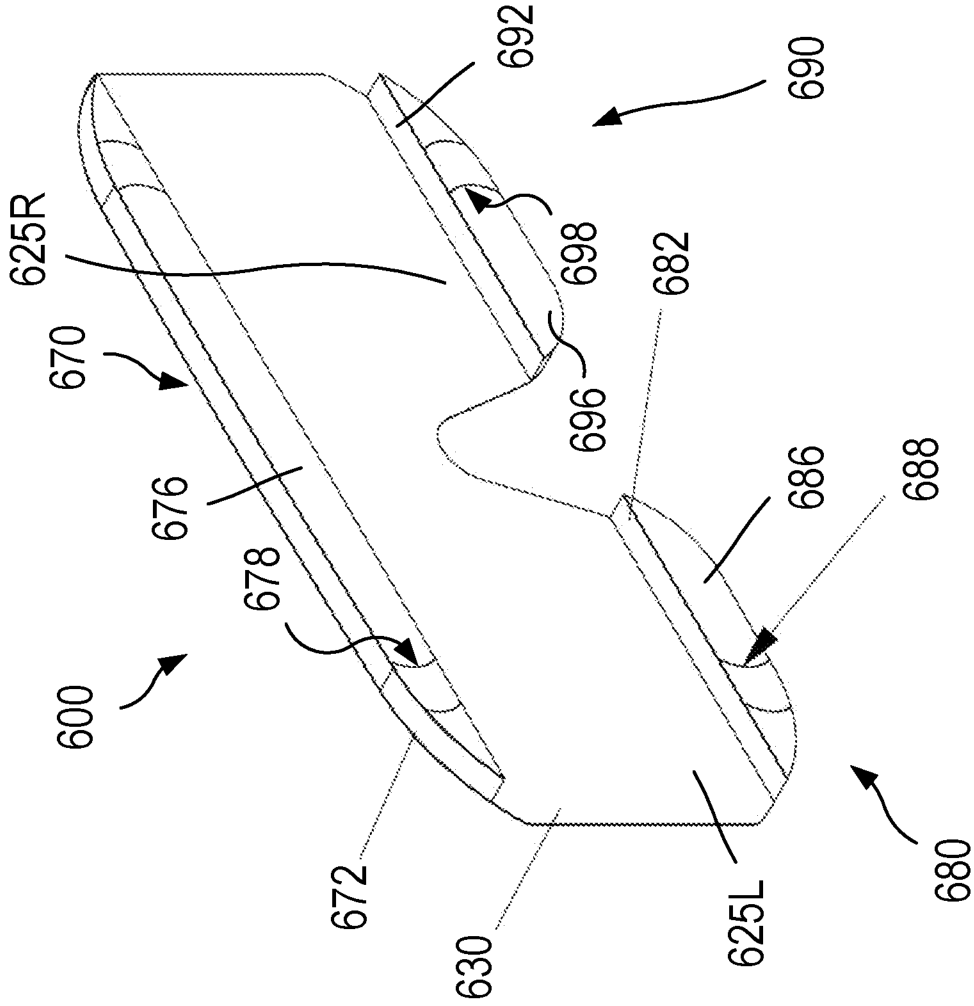

FIG. 6A provides a front perspective view of a wraparound eye shield device 600 and FIG. 6B provides a rear perspective view of wraparound eye shield device 600, according to embodiments of the present invention. As shown here, device 600 includes a shield body or main panel 630, an upper attachment assembly 670, a left lower attachment assembly 680, and a right lower attachment assembly 690. Upper attachment assembly 670 can include an upper compressible material 672, one or more upper adhesive materials (not shown), and an upper cover 676. As illustrated here, upper cover 676 can include one or more slits 678. Left lower attachment assembly 680 can include a lower left compressible material 682, one or more lower left adhesive materials (not shown), and a lower left cover 686. As illustrated here, lower left cover 686 can include one or more slits 688. Right lower attachment assembly 690 can include a lower right compressible material 692, one or more lower right adhesive materials (not shown), and a lower right cover 696. As illustrated here, lower right cover 696 can include one or more slits 698. Shield body or main panel 630 can include a notch 631 which is configured to rest upon and/or receive the nose bridge of the user or wearer. In exemplary embodiments, main panel or shield body 630 can include or be coupled with a right lower flap or zone 625R and a left lower flap or zone 625L which extend below the apex 632 of the notch 631. Left lower attachment assembly 680 can be coupled with a rear side of left lower flap or zone 625L, and right lower attachment assembly 690 can be coupled with a rear side of right lower flap or zone 625R. In some embodiments, a left lower flap or zone may be referred to as a left lower panel. In some embodiments, a right lower flap or zone may be referred to as a right lower panel. In exemplary embodiments, a main panel or shield body can include or be coupled with an upper flap or zone 615. Upper attachment assembly 670 can be coupled with a rear side of upper flap or zone 615. In some embodiments, an upper flap or zone may be referred to as an upper panel.

Figure 7:
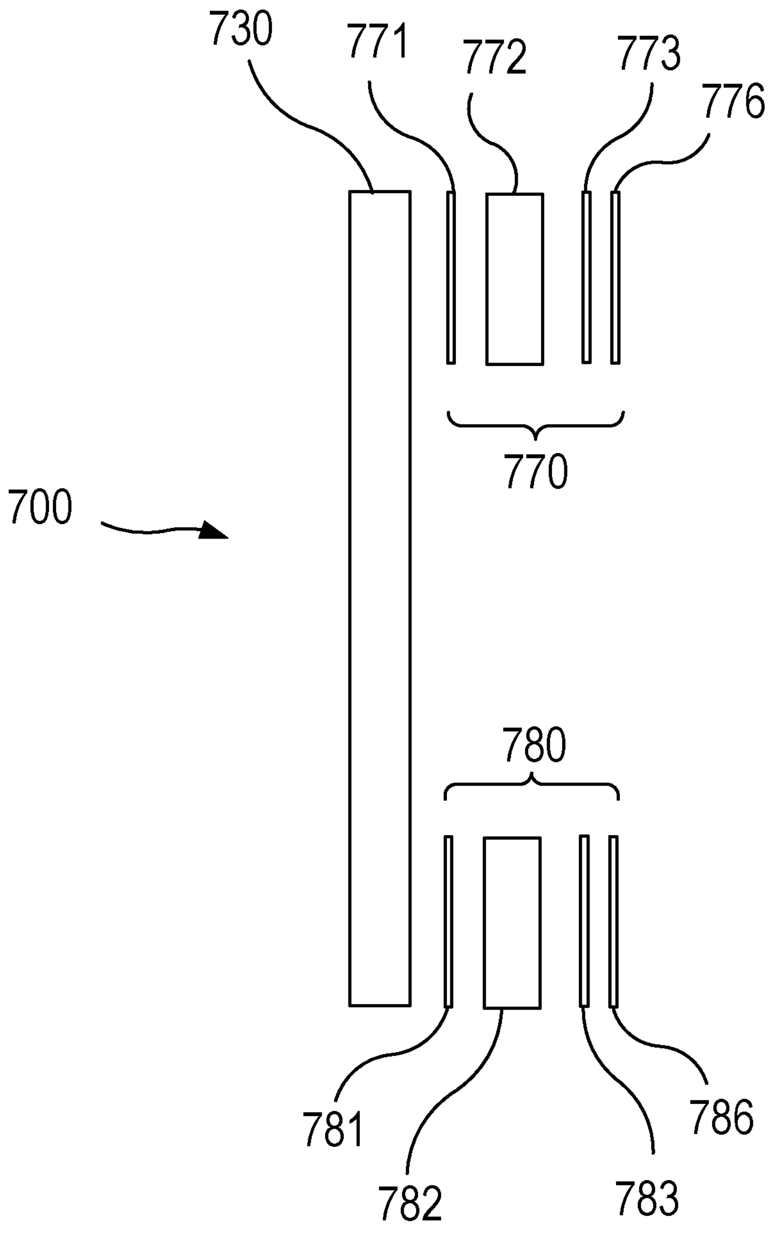
FIG. 7 illustrates aspects of wraparound eye shield systems and methods, according to embodiments of the present invention.

FIG. 7 provides an exploded cross section view of a wraparound eye shield device 700, according to embodiments of the present invention. As shown here, device 700 includes a shield body or main panel 730, an upper attachment assembly 770 and a lower attachment assembly 780 (right or left). Upper attachment assembly 770 can include a front or first adhesive material 771, an upper compressible material 772, a rear or second adhesive material 773, and an upper cover 776. In some cases, the second adhesive material 773 can be provided as a tape that is sticky or coated with adhesive on both sides, so that it adheres to both the compressible material 772 and to the wearer's face (not shown). In some cases, the second adhesive material can be provided as a double coated transfer tape. As discussed elsewhere herein, upper cover 776 can include one or more slits. Such slits can allow the user or wearer to peel back portions of the upper cover 776 needed or desired, so as to enable attachment or adherence between the underlying portions of the adhesive material 773 and the wearer's face. Lower attachment assembly 780 can include a front or first adhesive material 781, a lower compressible material 782, a rear or second adhesive material 783, and a lower cover 786. In some cases, the second adhesive material 783 can be provided as a tape that is sticky or coated with adhesive on both sides, so that it adheres to both the compressible material 782 and to the wearer's face (not shown). In some cases, the second adhesive material can be provided as a double coated transfer tape. As discussed elsewhere herein, lower cover 786 can include one or more slits. Such slits can allow the user or wearer to peel back portions of the lower cover 786 needed or desired, so as to enable attachment or adherence between the underlying portions of the adhesive material 783 and the wearer's face. In some cases, shield body or main panel 730 includes a polyester material. In some cases, shield body or main panel 730 can be provided as a coated polyester lens. In some cases, rear or second adhesive material (773 and/or 783) can be provided as a double coated transfer tape. In some cases, a shield device may have multiple upper attachment assemblies and/or multiple lower attachment assemblies. Advantageously, upper and/or lower attachment assemblies can help to provide enhanced protection for preventing splatter from getting into the patient's eyes, from above and/or below the main panel.

Figure 8:
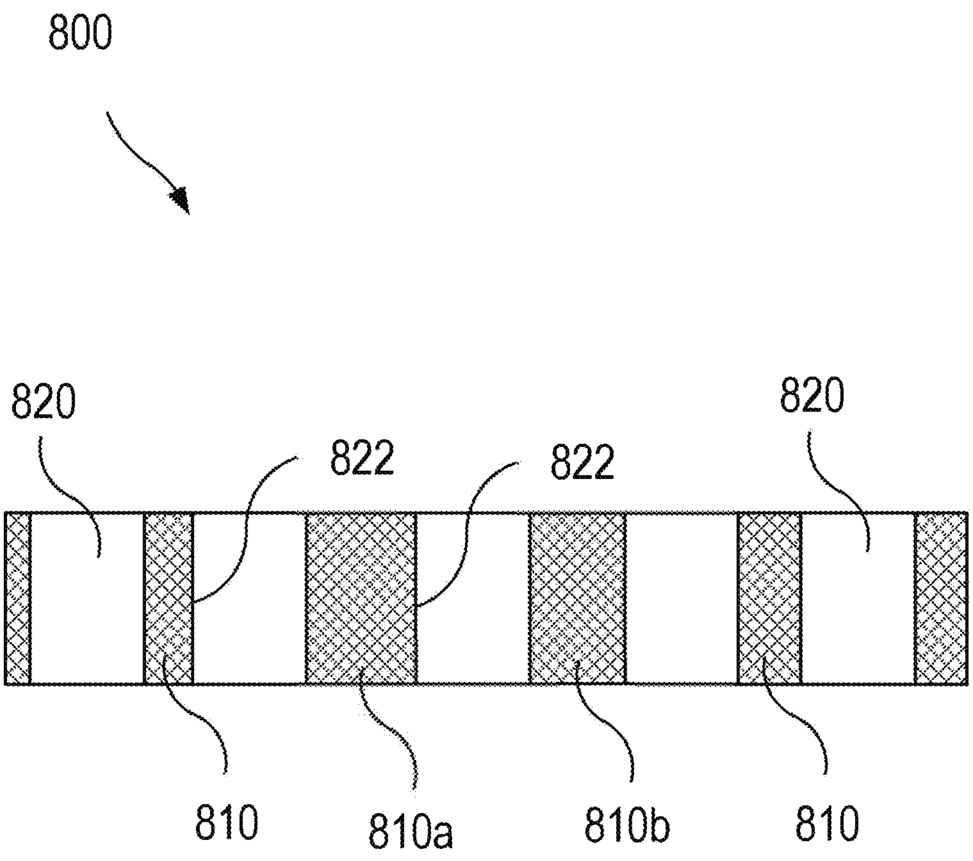
FIG. 8 illustrates aspects of wraparound eye shield systems and methods, according to embodiments of the present invention.

FIG. 8 provides a rear view of an attachment assembly 800, according to embodiments of the present invention. As shown here, attachment assembly 800 includes an adhesive material 810 that can be attached with an overlying cover 820. In some cases, a cover 820 can include one or more slits 822, thus providing one or more removable sections of cover 820 that can be peeled away or otherwise removed from the adhesive material, so as to expose corresponding underlying sections (e.g. 810*a*, 810*b*) of the adhesive material. By providing multiple slits, the user or wearer is enabled to expose the amount of adhesive area they wish to use, and/or the adhesive locations they wish to use, when adhering the shield device to their face.

Embodiments of the present invention are well suited for providing enhanced protection to a patient's eyes from splatter, spray, or other unwanted substances during dental procedures. Eyeshield devices can be provided with any degree of opacity, and may be configured to provide protection from damaging light, such as ultraviolet rays. In some embodiments, a shield body or main panel can include a clear material, a dark material, a green material, or an orange material. In some cases, an orange material for a shield body or main panel can operate to provide protection to the patient or wearer from ultraviolet light. In some cases, a shield body or main panel can include a material which provides protection for the patient or wearer from laser light. In some cases, a green material for a shield body or main panel can operate to provide protection to the patient or wearer from laser light. In some cases, the shield body or main panel can include material that protects the user or wearer from alexandrite laser light. In some cases, the shield body or main panel can include material that protects the user or wearer from diode laser light. In some cases, the shield body or main panel can include material that protects the user or wearer from ND:YAG laser light. In some cases, the shield body or main panel can include material that protects the user or wearer from laser light having a wavelength within a range from about 740 nm to about 1100 nm (and, for example, O.D 5+V.L.T 30%). In some cases, the shield body or main panel can include material that protects the user or wearer from laser light having a wavelength of 755 nm, 808 nm, 908 nm, 1064 nm, 1070 nm, or 1080 nm.

In some cases, wraparound eye shield devices can be used by outdoor enthusiasts or workers to prevent unwanted materials such as smoke, soot, dust, particles, foreign objects, cleaning chemicals, and the like from contacting their eyes. Wraparound eye shield device embodiments disclosed herein can also provide enhanced protection from the sun and wind.

Although embodiments of the present invention have been explained in relation to one or more preferred embodiments, it is to be understood that many other possible modifications and variations can be made without departing from the spirit and scope of the invention.

All features of the described systems and devices are applicable to the described methods mutatis mutandis, and vice versa. Embodiments of the present invention encompass kits having systems for filtering breathing air as disclosed herein. In some embodiments, the kit includes one or more eye shield devices, along with instructions for using the device or devices for example according to any of the methods disclosed herein. As described in this disclosure, in some embodiments the terms sub-portion and subsection may be used interchangeably.

Although the foregoing invention has been described in some detail by way of illustration and example for purposes of clarity of understanding, one of skill in the art will appreciate that certain changes, modifications, alternate constructions, and/or equivalents may be practiced or employed as desired, and within the scope of the appended claims. In addition, each reference provided herein is incorporated by reference in its entirety to the same extent as if each reference were individually incorporated by reference. Relatedly, all publications, patents, patent applications, journal articles, books, technical references, and the like mentioned in this specification are herein incorporated by reference to the same extent as if each individual publication, patent, patent application, journal article, book, technical reference, or the like was specifically and individually indicated to be incorporated by reference.

What is claimed is:

1. A wraparound eye shield device for a dental patient, comprising:

a main panel;

an upper panel extending above the main panel;

an upper score line between the main panel and the upper panel;

a left lower panel extending below the main panel;

a left lower score line between the main panel and the left lower panel, wherein the left lower score line enables the left lower panel to bend or curve relative to the main panel;

a right lower panel extending below the main panel;

a right lower score line between the main panel and the right lower panel, wherein the right lower score line enables the right lower panel to bend or curve relative to the main panel;

an upper attachment assembly coupled with the upper panel;

a left lower attachment assembly coupled with the left lower panel and located below the left lower score line;

and a right lower attachment assembly coupled with the right lower panel and located below the right lower score line;

wherein at least a portion of the left lower score line is parallel with at least a portion of the upper score line;

wherein at least a portion of the right lower score line is parallel with at least a portion of the upper score line;

wherein at least a portion of the left lower score line is colinear with at least a portion of the right lower score line;

wherein the upper attachment assembly includes an upper compressible material, an upper front adhesive material disposed between the upper panel and the upper compressible material, an upper cover having a plurality of slits, and an upper rear adhesive material disposed between the upper compressible material and the upper cover, wherein the left lower attachment assembly is configured to prevent splatter from getting into the dental patient's left eye from below the main panel during a dental procedure and includes a left lower compressible material, a left lower adhesive material disposed between the left lower panel and the left lower compressible material, a left lower cover having a plurality of slits, and a left lower rear adhesive material disposed between the left lower compressible material and the left lower cover, wherein the right lower attachment assembly is configured to prevent splatter from getting into the dental patient's right eye from below the main panel during a dental procedure and includes a right lower compressible material, a right lower adhesive material disposed between the right lower panel and the right lower compressible material, a right lower cover having a plurality of slits, and a right lower rear adhesive material disposed between the right lower compressible material and the right lower cover, and wherein at least one of the main panel, the upper panel, the left lower panel, and the right lower panel comprises a polyester material.

2. The wraparound eye shield device according to claim 1, wherein the main panel comprises the polyester material.

3. The wraparound eye shield device according to claim 1, wherein the upper panel comprises the polyester material.

4. The wraparound eye shield device according to claim 1, wherein the left lower panel comprises the polyester material.

5. The wraparound eye shield device according to claim 1, wherein the right lower panel comprises the polyester material.

6. The wraparound eye shield device according to claim 1, wherein the main panel, the upper panel, the left lower panel, and the right lower panel are constructed of a single continuous piece of the polyester material.

7. The wraparound eye shield device according to claim 1, wherein the upper compressible material comprises a polyurethane foam material.

8. The wraparound eye shield device according to claim 1, wherein the left lower compressible material comprises a polyurethane foam material.

9. The wraparound eye shield device according to claim 1, wherein the right lower compressible material comprises a polyurethane foam material.

10. The wraparound eye shield device according to claim 1, wherein at least one of the slits of the plurality of slits of the upper cover is a curved slit.

11. The wraparound eye shield device according to claim 1, wherein the polyester material is polyethylene terephthalate.

12. A wraparound eye shield device for a dental patient, comprising:

a main panel;

an upper panel extending above the main panel;

an upper score line between the main panel and the upper panel;

a left lower panel extending below the main panel;

a left lower score line between the main panel and the left lower panel, wherein the left lower score line enables the left lower panel to bend or curve relative to the main panel;

a right lower panel extending below the main panel;

a right lower score line between the main panel and the right lower panel, wherein the right lower score line enables the right lower panel to bend or curve relative to the main panel;

an upper attachment assembly coupled with the upper panel; a left lower attachment assembly coupled with the left lower panel and located below the left lower score line;

and a right lower attachment assembly coupled with the right lower panel and located below the right lower score line;

wherein at least a portion of the left lower score line is parallel with at least a portion of the upper score line;

wherein at least a portion of the right lower score line is parallel with at least a portion of the upper score line;

wherein at least a portion of the left lower score line is colinear with at least a portion of the right lower score line;

wherein the upper attachment assembly includes an upper compressible material, an upper front adhesive material disposed between the upper panel and the upper compressible material, an upper cover having a plurality of slits, and an upper double coated transfer tape disposed between the upper compressible material and the upper cover, wherein the left lower attachment assembly is configured to prevent splatter from getting into the dental patient's left eye from below the main panel during a dental procedure and includes a left lower compressible material, a left lower adhesive material disposed between the left lower panel and the left lower compressible material, a left lower cover having a plurality of slits, and a left lower rear double coated transfer tape disposed between the left lower compressible material and the left lower cover, wherein the right lower attachment assembly is configured to prevent splatter from getting into the dental patient's right eye from below the main panel during a dental procedure and includes a right lower compressible material, a right lower adhesive material disposed between the right lower panel and the right lower compressible material, a right lower cover having a plurality of slits, and a right lower rear double coated transfer tape disposed between the right lower compressible material and the right lower cover, and wherein at least one of the main panel, the upper panel, the left lower panel, and the right lower panel comprises a polyester material.

13. The wraparound eye shield device according to claim 12, wherein the main panel comprises the polyester material.

14. The wraparound eye shield device according to claim 12, wherein the upper panel comprises the polyester material.

15. The wraparound eye shield device according to claim 12, wherein the left lower panel comprises the polyester material.

16. The wraparound eye shield device according to claim 12, wherein the right lower panel comprises the polyester material.

17. The wraparound eye shield device according to claim 12, wherein the main panel, the upper panel, the left lower panel, and the right lower panel are constructed of a single continuous piece of the polyester material.

18. The wraparound eye shield device according to claim 12, wherein the upper compressible material comprises a polyurethane foam material.

19. The wraparound eye shield device according to claim 12, wherein the left lower compressible material comprises a polyurethane foam material.

20. The wraparound eye shield device according to claim 12, wherein the right lower compressible material comprises a polyurethane foam material.

21. The wraparound eye shield device according to claim 12, wherein at least one of the slits of the plurality of slits of the upper cover is a curved slit.

22. The wraparound eye shield device according to claim 12, wherein the polyester material is polyethylene terephthalate.

* * * * *